United States Patent [19]

Steer

[11] Patent Number: 4,964,856
[45] Date of Patent: Oct. 23, 1990

[54] SECURING AN OUTLET PIPE OR TAP TO A LIQUID-CONTAINING BAG

[75] Inventor: Peter L. Steer, Surrey, England

[73] Assignee: E. R. Squibb & Sons, Inc., Princeton, N.J.

[21] Appl. No.: 440,488

[22] Filed: Nov. 24, 1989

Related U.S. Application Data

[63] Continuation of Ser. No. 203,845, Jun. 8, 1988, abandoned.

[30] Foreign Application Priority Data

Jun. 18, 1987 [GB] United Kingdom ............... 87 14303

[51] Int. Cl.$^5$ ............................................. A61M 1/00
[52] U.S. Cl. .................................................. 604/326
[58] Field of Search ............... 604/323, 326, 335, 350; 383/36, 904, 906; 285/347, 332, DIG. 921; 222/522, 525; 251/340

[56] References Cited

U.S. PATENT DOCUMENTS

| | | | |
|---|---|---|---|
| 3,322,590 | 5/1967 | Clark | 156/273 |
| 3,394,954 | 7/1968 | Sarns | 285/319 |
| 3,558,397 | 1/1971 | Clark | 156/272 |
| 3,881,486 | 5/1975 | Fenton | 128/283 |
| 4,089,131 | 5/1978 | Phillips | 285/260 |
| 4,278,276 | 7/1981 | Ekman | 285/49 |
| 4,300,560 | 11/1981 | Steer et al. | 128/283 |
| 4,462,510 | 7/1984 | Steer et al. | 222/48 |
| 4,475,907 | 10/1984 | Voges | 604/322 |
| 4,534,766 | 8/1985 | Steer et al. | 604/323 |
| 4,580,816 | 4/1986 | Campbell et al. | 285/321 |

FOREIGN PATENT DOCUMENTS

| | | |
|---|---|---|
| 2135652 | 1/1984 | European Pat. Off. . |
| 1041753 | 10/1958 | Fed. Rep. of Germany ...... 285/332 |
| 2249406 | 10/1972 | Fed. Rep. of Germany . |
| 2076932 | 1/1971 | France . |
| 543733 | 5/1942 | United Kingdom . |
| 871820 | 12/1957 | United Kingdom . |
| 1332447 | 4/1972 | United Kingdom . |
| 2126483 | 7/1983 | United Kingdom . |
| 2191757 | 12/1987 | United Kingdom . |

Primary Examiner—David J. Isabella
Attorney, Agent, or Firm—Stephen B. Davis

[57] ABSTRACT

An outlet pipe or tap is secured to a liquid containing bag by trapping the bag outlet region between inner and outer nested funnels. A leak proof seal is provided by disposing an O-ring sealing means between the funnels and moving one funnel axially relative to the other.

1 Claim, 2 Drawing Sheets

SECURING AN OUTLET PIPE OR TAP TO A LIQUID-CONTAINING BAG

This is a continuation of copending application Ser. No. 203,845 filed on June 8, 1988 now abandoned.

BACKGROUND OF THE INVENTION

Fluid containers or bags designed for medical applications conventionally include an outlet pipe or tap to drain the container. One such type of bag is a urostomy pouch such as shown by Steer et al. in U.S. Pat. No. 4,300,560 having a valve assembly welded in place. Another type of valve assembly including an O-ring is shown by Steer in United Kingdom Patent Application No. 2,191,757.

Other types of urine collecting bags including an outlet pipe or tap are collection receptacles of a urinary incontinence system such as the leg bag shown by Steer et al. in U.S. Pat. No. 4,462,510 and the hanging bag shown by Steer et al. in U.S. Pat. No. 4,534,766.

SUMMARY OF THE INVENTION

This invention relates to a bag for containing liquids and to securing an outlet pipe or tap to a liquid-containing bag.

According to the invention, a method of securing an outlet pipe or tap to a bag for containing a liquid, such as urine, involves using a pair of nested funnels, disposing a bag outlet region between the funnels, and providing a liquid seal by disposing O-ring sealing means between the funnels and moving one funnel axially relative to the other in order to trap the bag outlet region between the funnels.

In a preferred version of the invention, the outer funnel has an annular recess, of a cross-sectional shape complementary to the O-ring sealing means, in its inner surface. This recess locates the O-ring sealing means definitely when one funnel is moved relative to the other.

The O-ring sealing means may be a simple O-ring or it may be a peripheral projection integral with the inner funnel. The outlet region of the bag is preferably permanently secured, e.g., by heat welding, RF welding or ultrasonic welding, to the inner funnel.

The O-ring sealing means may be located on a tapering portion or on a parallel-sided portion of the funnel, the latter being preferred.

In an alternative embodiment of the invention, the same principle may be employed but the O-ring sealing means could be an annular projection projecting inwardly from the inner surface of the outer funnel and the annular recess may be a recess in the outer wall of the inner funnel.

This invention is also directed to the bag itself. That is, the invention also consists in a bag for containing liquid including an outlet region trapped in a leakproof manner between a nested pair of members which are complementarily tapered. The invention further consists in such a bag which also has embodied therein O-ring sealing means located between the nested members.

BRIEF DESCRIPTION OF THE DRAWINGS

The invention will be better understood from the following non-limiting description of two examples thereof given with reference to the accompanying drawings, in which.

DETAILED DESCRIPTION OF THE INVENTION

Figure 1:
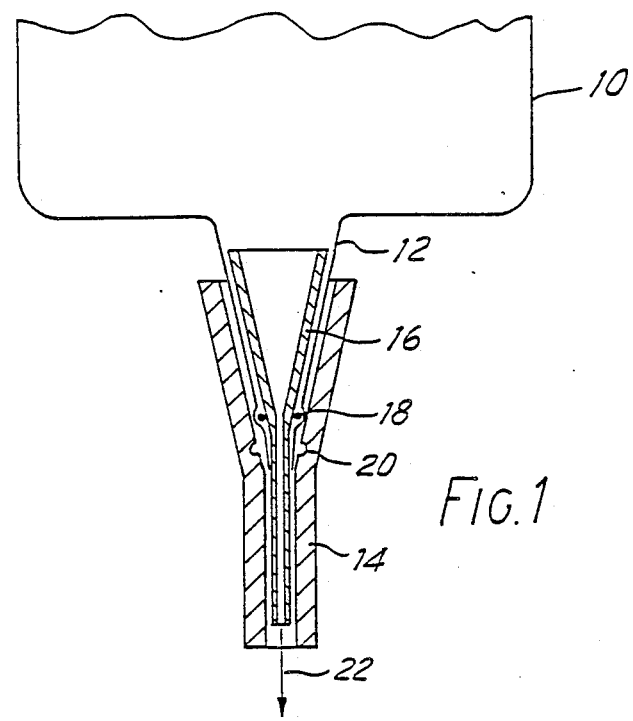
FIG. 1 is a diagrammatic sketch cross-sectional view of a bag for containing liquid.

As shown in FIG. 1, the bag 10 for containing liquids includes an outlet region 12 whose walls are trapped between outer funnel 14 and inner funnel 16. An O-ring 18 is provided to be received in annular recess 20 in the inner wall of outer funnel 14.

The parts are shown in their relative positions just prior to final assembly, which is effected by pushing the funnel 16 axially relative to the funnel 14 so that it is fully nested and the O-ring 18 is lodged substantially within the recess 20. The liquid exit path is shown by the arrow 22. As will be seen, the only theoretically available leakage path is down the outer surface of the inner funnel, past the compressed O-ring, and up the inner surface of the outer funnel. Leakage is hence virtually impossible.

Figure 3:
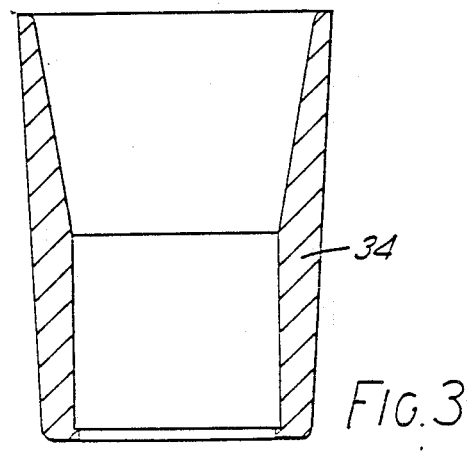
FIGS. 2–4 are cross sections illustrating the preferred embodiment of the invention.
Figure 2:
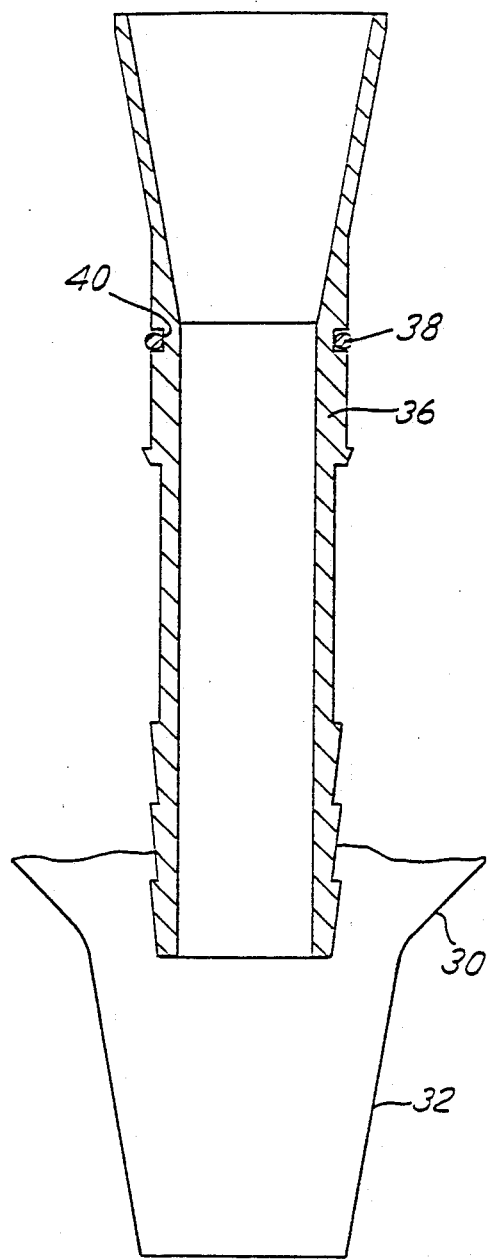
Figure 4:
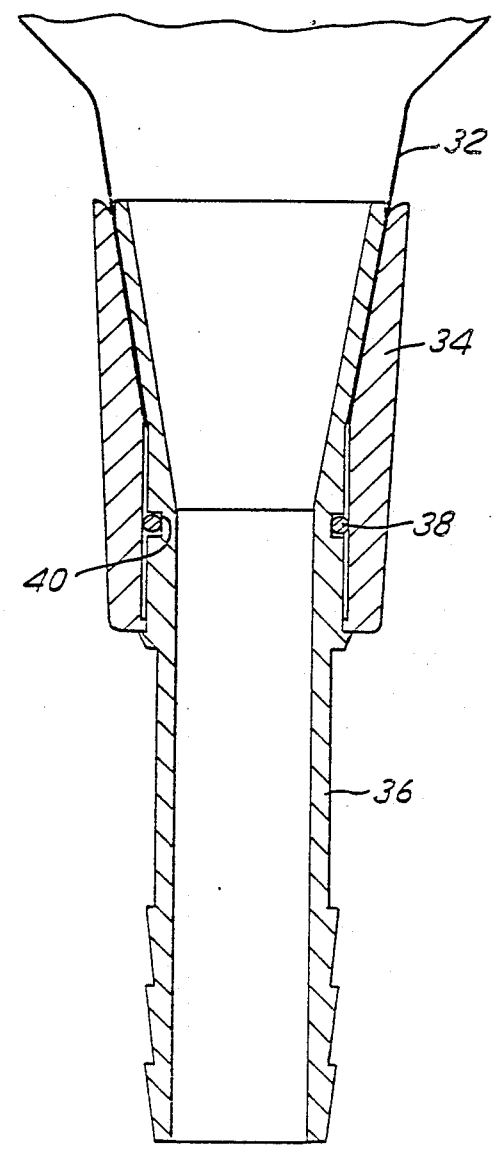

The parts of the embodiment of the invention shown in FIGS. 2–4 are as follows. This embodiment employs the same principle as the FIG. 1 embodiment. The bag 30 for containing liquid has an outlet region 32. An outer funnel 34 and an inner funnel 36 are provided between which the bag walls of outlet region 32 are trapped. An O-ring sealing means 38 is located on the parallel-sided portion of inner funnel 36 beneath the outward tapered region. The O-ring 38 is accomodated within an annular recess 40 in the outer wall of inner funnel 36. The portion of the inner funnel 36, as shown in FIG. 4, which extends beyond the outer funnel 34 when the parts are asembled includes a series of sawteeth on its outer wall to permit tubing to be slid over this portion of the inner funnel.

Figure 5:
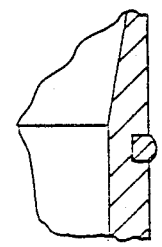
FIG. 5 is a scrap section showing an alternative in which an O-ring sealing means is molded in position in an annular channel in the external surface of the inner funnel.

As seen in FIG. 5, instead of a separate O-ring, one can be initially molded in position in the annular channel or recess.

The funnels may be made of any suitable material, e.g., a synthetic plastics material such as polyester. This may be molded. In some circumstances a pair of metal funnels may be employed. It is desirable, but not essential to weld the bag outlet region to the inner funnel.

As will be seen from the foregoing description, on the inner funnel molding there is fitted a parallel exit tube below the tapering portion. An O-ring is disposed around the parallel portion or there may be an injection molded soft ring. The bag film finishes on the taper, and the two components squash the O-ring in between them so that there cannot be a leak path at that point. The purpose and advantage of the taper is that the very action of pushing on the outer funnel to deform the sealing means on the inner funnel tends to force the bag material up the taper thus tightening its grip around the molding.

The upper portions of bags 10 and 30 are not shown. These upper portions could, for example, be of a urostomy configuration as shown in U.S. Pat. No. 4,300,560 or of a leg bag configuration as shown in U.S. Pat. No. 4,462,510.

While the term funnel has been employed in this description, it will be appreciated that co-operating parts of non-circular cross section might be employed as an alternative.

What is claimed is:

1. A bag for containing liquid including an outlet region trapped in a leakproof manner between a nested pair of members which are complementarily tapered, said nested pair of members comprising inner and outer funnel members having outwardly tapered portions and parallel portions, said bag outlet region being trapped between said inner and outer funnel members in the area of said outward tapers, said parallel portion of said outer funnel means extending below the parallel portion of said inner funnel means.

* * * * *